US00PP28257P3

(12) United States Plant Patent
Verwer

(10) Patent No.: US PP28,257 P3
(45) Date of Patent: Aug. 8, 2017

(54) ***DAHLIA* PLANT NAMED 'HDBIC34'**

(50) Latin Name: *Dahlia hybrida*
Varietal Denomination: HDBic34

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 51 days.

(21) Appl. No.: 14/545,627

(22) Filed: May 29, 2015

(65) Prior Publication Data

US 2016/0353641 P1 Dec. 1, 2016

(51) Int. Cl.
*A01H 5/02* (2006.01)

(52) U.S. Cl.
USPC ..... Plt./321

(58) Field of Classification Search
USPC ..... Plt./321
See application file for complete search history.

(56) References Cited

PUBLICATIONS

Campbell's Greenhouses 2014 New Varieties retrieved on Sep. 15, 2016, retrieved from the Internet at <http://www.campbellsgreenhouses.com/images/2014_new_varieties.pdf> p. 15-16.*

Verwer Dahlias Happy Days *Dahlia* retrieved on Sep. 15, 2016, retrieved from the Internet at http://www.verwer-dahlias.com/hdays/bico_en.html one page.*

WW Greenhouses Annual Varieties for 2013 (revised Apr. 2018) retrieved on Sep. 15, 2016, retrieved from the Internet at <http://www.wwgreenhouses.com/images/images_misc/2013annualcontents_041813.pdf> pp. 1-18.*

W.W. Greenhouses Plant listing and availability retrieved on Sep. 15, 2016, retrieved from the Internet at <http://www.wwgreenhouses.com/more-info/plant-listings.html> one page.*

* cited by examiner

*Primary Examiner* — June Hwu
(74) *Attorney, Agent, or Firm* — C. A. Whealy

(57) ABSTRACT

A new and distinct cultivar of *Dahlia* plant named 'HDBic34', characterized by its compact, mounding and dense plant habit; freely basal branching habit; dark-colored leaves; early and freely flowering habit; daisy-type inflorescence form; large inflorescences with red and yellow bi-colored ray florets; and good postproduction longevity.

2 Drawing Sheets

Botanical designation: *Dahlia hybrida.*
Cultivar denomination: 'HDBic34'.

BACKGROUND OF THE INVENTION

The present invention relates to a new and distinct cultivar of *Dahlia* plant, botanically known as *Dahlia hybrida*, and hereinafter referred to by the name 'HDBic34'.

The new *Dahlia* plant is a product of a planned breeding program conducted by the Inventor in Lisse, The Netherlands. The objective of the breeding program is to create new compact container *Dahlia* plants with dark-colored leaves, large inflorescences and good postproduction longevity.

The new *Dahlia* plant originated from an open-pollination in 2009 of a proprietary seedling selection of *Dahlia hybrida* identified as code number VD5-272, not patented, as the female, or seed, parent with an unknown selection of *Dahlia hybrida* as the male, or pollen, parent. The new *Dahlia* plant was discovered and selected by the Inventor as a single flowering plant from within the progeny of the stated open-pollination in a controlled greenhouse environment in Lisse, The Netherlands in 2010.

Asexual reproduction of the new *Dahlia* plant by stem cuttings since the spring of 2011 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'HDBic34'. These characteristics in combination distinguish 'HDBic34' as a new and distinct *Dahlia* plant:

1. Compact, mounding and dense plant habit.
2. Freely basal branching habit.
3. Dark-colored leaves.
4. Early and freely flowering habit.
5. Daisy-type inflorescence form.
6. Large inflorescences with red and yellow bi-colored ray florets.
7. Good postproduction longevity.

Plants of the new *Dahlia* differ primarily from plants of the female parent selection in the following characteristics:

1. Plants of the new *Dahlia* are more compact than plants of the female parent selection.
2. Plants of the new *Dahlia* are denser than and not as open as plants of the female parent selection.
3. Plants of the new *Dahlia* and the female parent selection differ in ray floret color as plants of the female parent selection have brownish red and pale creamy white bi-colored ray florets.

Plants of the new *Dahlia* can be compared to plants of the *Dahlia hybrida* 'HDRF155', disclosed in U.S. Plant Pat. No. 23,300. In side-by-side comparisons conducted in Lisse, The Netherlands, plants of the new *Dahlia* differed from plants of 'HDRF155' in the following characteristics:

1. Plants of the new *Dahlia* were taller than plants of 'HDRF155'.
2. Plants of the new *Dahlia* were more freely branching than plants of 'HDRF155'.
3. Plants of the new *Dahlia* had thicker stems than plants of 'HDRF155'.
4. Plants of the new *Dahlia* flowered two days earlier than plants of 'HDRF155'.
5. Plants of the new *Dahlia* and 'HDRF155' differed in ray color as plants of 'HDRF155' had red and orange bi-colored ray florets.
6. Plants of the new *Dahlia* had longer peduncles than plants of 'HDRF155'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'HDBic34' grown in an outdoor nursery.

The photograph on the second sheet is a close-up view of a typical flowering plant of 'HDBic34'.

DETAILED BOTANICAL DESCRIPTION

The photographs and following observations and measurements describe plants grown during the late summer and early autumn in ground beds in an outdoor nursery in Lisse, The Netherlands and under cultural practices typical of commercial *Dahlia* production. During the production of the plants, day temperatures ranged from 12° C. to 29° C. and night temperatures ranged from 6° C. to 19° C. Plants were pinched one time about three weeks after planting. Plants were four months old when the photographs were taken and three months old when the description was taken. In the following description, color references are made to The Royal Horticultural Society Colour Chart, 1995 Edition, except where general terms of ordinary dictionary significance are used.

Botanical classification: *Dahlia hybrida* 'HDBic34'.

Parentage:

*Female, or seed, parent*.—Proprietary seedling selection of *Dahlia hybrida* identified as code number VD5-272, not patented.

*Male, or pollen, parent*.—Unknown selection of *Dahlia hybrida*, not patented.

Propagation:

*Type*.—By vegetative stem cuttings.

*Time to initiate roots, summer*.—About 13 days at soil temperatures about 15° C. and air temperatures about 22° C.

*Time to initiate roots, winter*.—About 14 days at soil temperatures about 15° C. and air temperatures about 22° C.

*Time to produce a rooted young plant, summer*.—About 20 days at soil temperatures about 15° C. and air temperatures about 22° C.

*Time to produce a rooted young plant, winter*.—About 24 days at soil temperatures about 15° C. and air temperatures about 23° C.

*Root description*.—Fine, fleshy; white in color.

*Rooting habit*.—Moderately freely branching; dense.

*Tubers*.—Length: About 16 cm. Diameter: About 14 cm. Texture: Corky. Color: Close to 199B.

Plant description:

*Plant and growth habit*.—Compact and mounding plant habit; appropriate for 16-cm to 18-cm containers; inverted triangular plant form; freely basal branching with about eight primary lateral branches developing per plant; dense and bushy appearance; inflorescences held above the foliar plane on strong peduncles; vigorous growth habit.

*Plant height*.—About 35 cm.

*Plant diameter or spread*.—About 30 cm.

*Lateral branches*.—Length: About 30 cm. Diameter: About 2 cm. Internode length: About 6 cm to 12 cm. Texture: Smooth, glabrous. Strength: Strong. Aspect: Erect to about 20° from vertical. Color: Close to 146A tinged with close to 200A.

Leaf description:

*Arrangement*.—Opposite, simple or compound with three or five leaflets per leaf.

*Leaf length, simple leaves*.—About 7 cm.

*Leaf width, simple leaves*.—About 3.5 cm.

*Leaf length, compound leaves with three leaflets*.—About 18 cm.

*Leaf width, compound leaves with three leaflets*.—About 13 cm.

*Leaf length, compound leaves with five leaflets*.—About 23 cm.

*Leaf width, compound leaves with five leaflets*.—About 11 cm.

*Shape, simple leaves or leaflets*.—Ovate.

*Apex, simple leaves or leaflets*.—Acuminate.

*Base, simple leaves or leaflets*.—Attenuate.

*Margin, simple leaves or leaflets*.—Serrate; sinuses divergent.

*Venation pattern, simple leaves or leaflets*.—Pinnate, reticulate.

*Texture, upper and lower surfaces, simple leaves or leaflets*.—Smooth, glabrous.

*Color*.—Developing and fully expanded leaves or leaflets, upper surface: Close to 147A; leaves and leaflets that are exposed to higher light levels (upper and outermost leaves and leaflets) are heavily tinged with close to 200B; venation, close to 184B. Developing and fully expanded leaves or leaflets, lower surface: Darker than 191A; color becoming closer to 191A with development; venation, close to 152B.

*Petioles*.—Length, simple leaves: About 1 cm. Length, compound leaves with three leaflets: About 4 cm. Length, compound leaves with five leaflets: About 7 cm. Diameter, simple leaves or leaflets: About 2 mm. Texture, upper and lower surfaces, simple leaves or leaflets: Smooth, glabrous. Color, simple leaves or leaflets: Upper surface: Close to 184B. Lower surface: Close to 152B; outermost leaves and leaflets, close to 174B.

Inflorescence description:

*Appearance and flowering habit*.—Daisy-type inflorescences with ray and disc florets developing acropetally on a receptacle; inflorescences positioned above and beyond the foliar plane on strong peduncles; inflorescences face upright to outwardly; freely flowering habit with typically about 40 inflorescences developing per plant.

*Fragrance*.—None detected.

*Time to flower*.—Early flowering habit; plants begin flowering about 65 days after planting; flowering continuous during the summer and autumn in The Netherlands.

*Post-production longevity*.—Good postproduction longevity; inflorescences maintain good substance for about 16 days on the plant and for about five days as a cut flower; inflorescences persistent.

*Inflorescence buds*.—Height: About 1.5 cm. Diameter: About 1.7 cm. Shape: Oblate. Texture: Smooth, glabrous. Color: Close to 200B.

*Inflorescence diameter*.—About 9.3 cm.

*Inflorescence depth* (*height*).—About 2 cm.

*Disc diameter*.—About 2 cm.

*Receptacle height*.—About 1.7 cm.

*Receptacle diameter*.—About 1.6 cm.

*Receptacle color*.—Darker than 187A.

*Ray florets*.—Number of ray florets per inflorescence: About eight arranged in a single whorl. Length: About 4.9 cm. Width: About 2.4 cm. Shape: Ovate. Apex: Obtuse. Base: Attenuate. Margin: Entire, Aspect: Initially upright to roughly perpendicular to the peduncle. Texture, upper and lower surfaces: Smooth, glabrous; velvety. Color: When opening, upper surface: Close to 46A; towards the apex, close to 17A. When opening, lower surface: Close to 46A; towards the apex, close to 161A; along the veins, close to 161A. Fully opened, upper surface: Close to 45A; towards the apex, close to 14A; color does not fade with development. Fully opened, lower surface: Close to 44A; towards the apex, close to 20A; color does not fade with development.

*Disc florets*.—Number of disc florets per inflorescence: About 100. Length: About 1.5 cm. Diameter: About 1 mm. Shape: Tubular; apex dentate. Aspect: Mostly upright. Texture: Smooth, glabrous. Color, immature: Apex: Close to 200A. Mid-section: Close to 175A. Base: Close to 151A. Color, mature: Apex: Close to 21A. Mid-section: Close to 175A. Base: Close to 21A.

*Phyllaries*.—Quantity per inflorescence: About five or six arranged in a single whorl. Length: About 1.5 cm. Width: About 4 mm. Shape: Ovate to lanceolate. Apex: Acute. Base: Attenuate. Margin: Entire. Texture, upper and lower surfaces: Smooth, glabrous. Color, upper and lower surfaces: Close to 200A.

*Peduncles*.—Length, terminal peduncle: About 23 cm. Length, fourth peduncle: About 14 cm. Length, seventh peduncle: About 8 cm. Diameter: About 6 mm. Strength: Strong. Aspect: Mostly erect to 20° from vertical. Texture: Smooth, glabrous. Color: Close to 200A.

*Reproductive organs*.—Androecium, present on disc florets only: Quantity per disc floret: Five. Filament length: About 4 mm. Filament color: Close to 3B. Anther length: About 2 mm. Anther shape: Lanceolate. Anther color: Close to 15A. Pollen amount: Moderate. Pollen color: Close to 20B. Gynoecium, present on ray and disc florets: Quantity per floret: One. Pistil length: About 3 mm. Stigma shape: Lanceolate. Stigma color: Close to 12C. Style length: About 5 mm. Style color: Close to 150B. Ovary color: Close to 150C. Fruits: Length: About 1.6 cm. Diameter: About 1.5 cm. Texture: Smooth, glabrous. Color: Close to 200A. Seeds: Quantity per fruit: About 25. Length: About 5 mm. Diameter: About 0.8 mm. Color: Close to 187A.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 40° C.

It is claimed:

1. A new and distinct *Dahlia* plant named 'HDBic34' as illustrated and described.

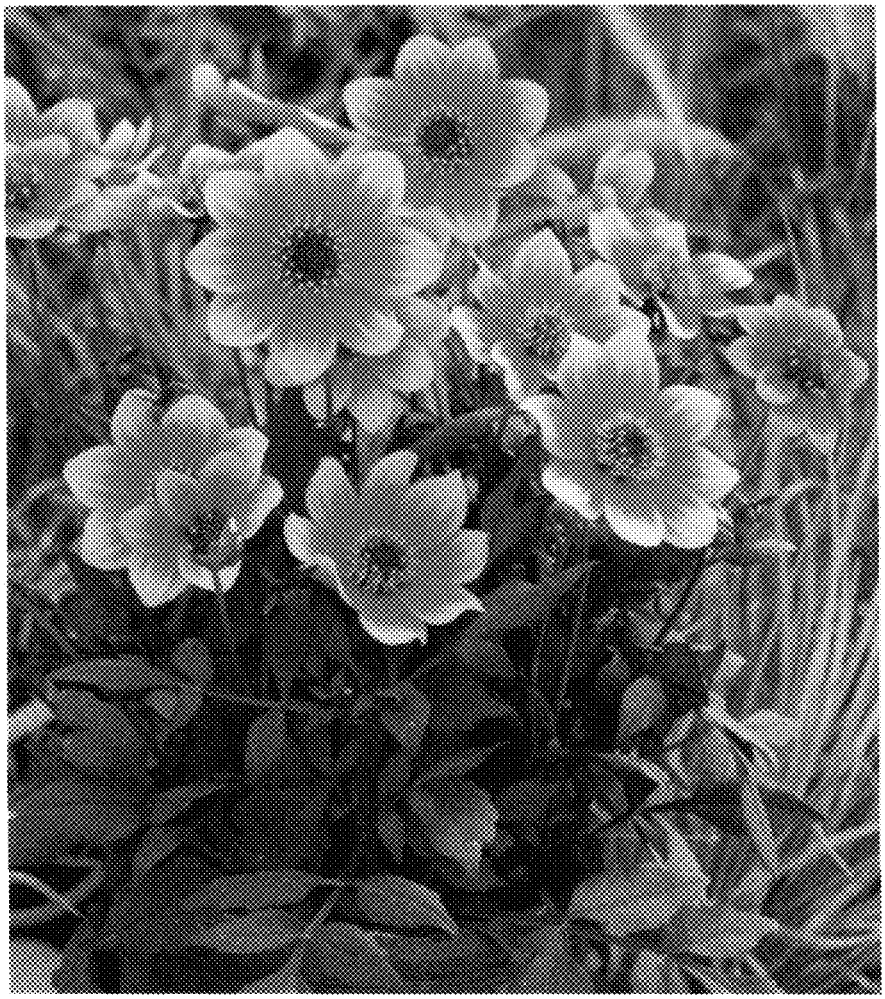

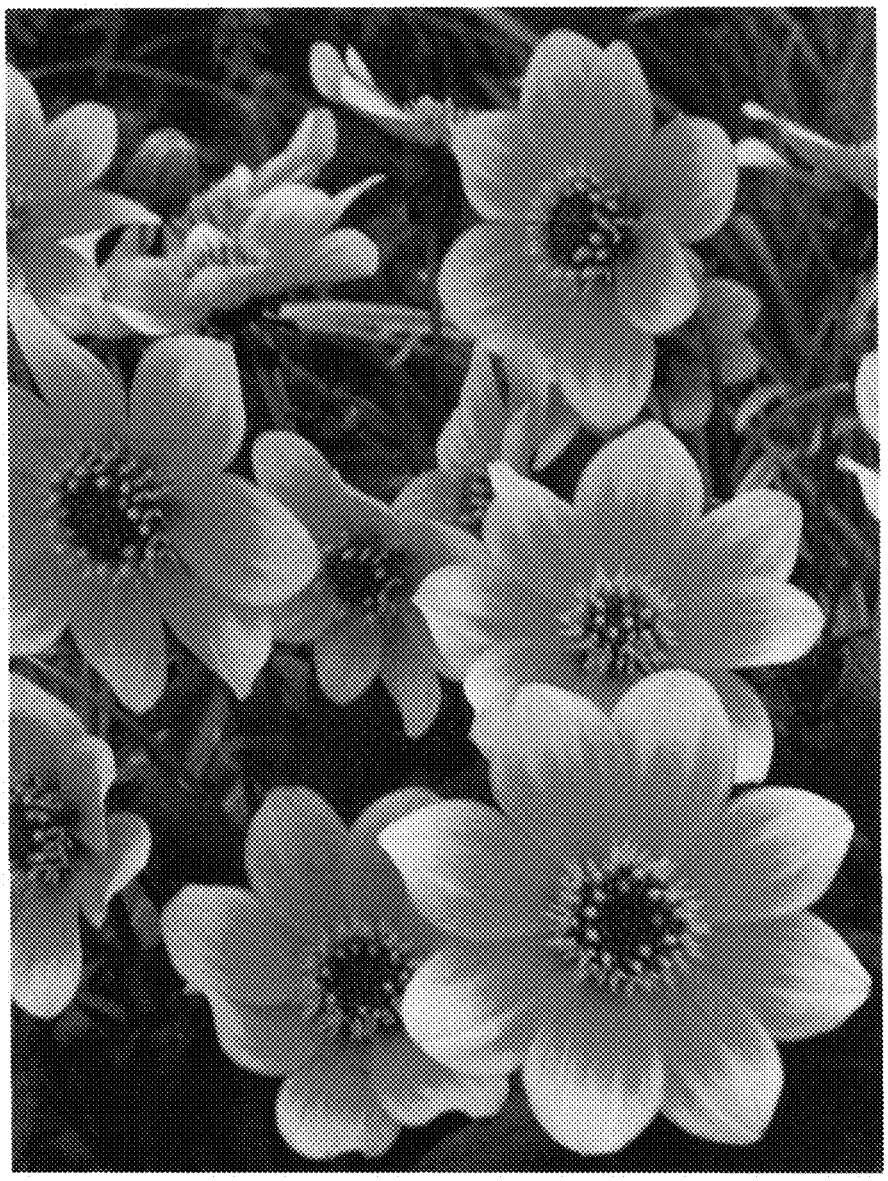

* * * * *